United States Patent [19]
Bandiera et al.

[11] Patent Number: 6,103,700
[45] Date of Patent: Aug. 15, 2000

[54] FLUORO LABELLED ANTHRACYCLINONE AND ANTHRACYCLINE DERIVATIVES

[75] Inventors: Tiziano Bandiera, Gambolò ; Daniele Fancelli, Milan; Michele Caruso, Milan; Jacqueline Lansen, Milan; Antonino Suarato, Milan, all of Italy

[73] Assignee: Pharmacia & Upjohn S.p.A., Milan, Italy

[21] Appl. No.: 09/202,954

[22] PCT Filed: Jun. 18, 1997

[86] PCT No.: PCT/EP97/03234

§ 371 Date: Dec. 14, 1998

§ 102(e) Date: Dec. 14, 1998

[87] PCT Pub. No.: WO97/49433

PCT Pub. Date: Dec. 31, 1997

[30] Foreign Application Priority Data

Jun. 26, 1996 [GB] United Kingdom ................... 9613433

[51] Int. Cl.$^7$ .................. A61K 31/70; A61K 31/495; C07D 295/185; C07D 295/26; C07D 295/104
[52] U.S. Cl. ............. 514/34; 514/255; 514/656; 536/6.4; 552/296
[58] Field of Search ............. 514/34, 255, 656; 536/6.4; 552/296

[56] References Cited

U.S. PATENT DOCUMENTS 5,731,313  3/1998  Suarato et al. ................... 514/255
5,744,454  4/1998  Suarato et al. ................... 514/34

FOREIGN PATENT DOCUMENTS

07665/96  3/1996  WIPO .

*Primary Examiner*—Mukund J. Shah
*Assistant Examiner*—Pavanaram K Sripada
*Attorney, Agent, or Firm*—Oblon, Spivak, McClelland, Maier & Neustadt, P.C.

[57] ABSTRACT

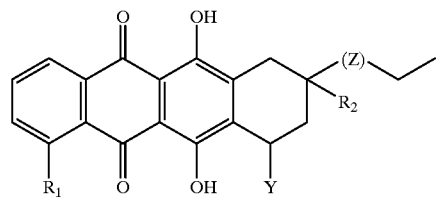

Compounds of formula (A), wherein $R_1$, $R_2$, $R_3$, Y and Z are organic substituents, are useful in the diagnosis of amyloidosis; some of the compounds of formula (A) are novel. Processes for their preparation, and pharmaceutical compositions containing them are also described.

8 Claims, No Drawings

FLUORO LABELLED ANTHRACYCLINONE AND ANTHRACYCLINE DERIVATIVES

This application is a 371 of PCT/EP 97/03234, Jun. 18, 1997.

The present invention relates to the use of fluoro anthracyclinone and fluoro anthracycline derivatives as NMR imaging probes for monitoring amyloidotic diseases. The term amyloidosis indicates various diseases whose common characteristic is the tendency of particular proteins to aggregate and precipitate, as insoluble fibrils, into the extracellular space causing structural and functional damage to organs and tissues. The classification of amyloid and amyloidosis has been recently revised in Bulletin of the World Health Organisation 71(1): 105 (1993). All the different types of amyloid share the same ultrastructural organisation in anti-parallel β-pleated sheets despite the fact that they contain a variety of widely differing protein subunits [see: Glenner G. G., New England Journal of Medicine 1980, vol. 302, p. 1283; Ghiso J. et al., Molecular Neurobiology 1994, vol. 8, p. 49].

The clinical course of the disease depends on the selectivity of organ involvement; the prognosis can be extremely unfavourable in case of heart infiltration (median survival <12 months) or more benign in case of kidney involvement (median survival approx. 5 years). The compounds of the formula A are able to interact with amyloid deposits and plaques and with fibrils of amyloid. Accordingly the present invention provides the use of a compound which is an anthracycline or anthracyclinone derivative of the general formula A:

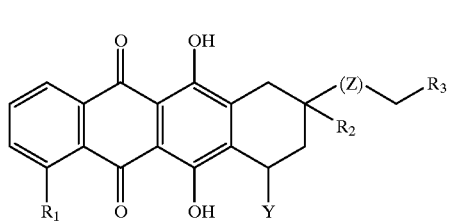

A wherein:

$R_1$ is hydrogen, hydroxyl, halogen, $C_1$–$C_8$ alkoxyl, amino which may be substituted by benzyl, acyl or trifluoroacetyl, or $OSO_2$ ($R_4$), wherein $R_4$ is alkyl or aryl, each of which is unsubstituted or substituted by one or more fluorine atoms;

$R_2$ is hydrogen or hydroxy;

$R_3$ is hydrogen, hydroxyl, amino which may be mono- or di-substituted by $C_1$–$C_{16}$ alkyl, aryl, aralkyl, $C_2$–$C_8$ alkenyl, $C_3$–$C_8$ cycloalkyl, $C_5$–$C_8$ cyclo-alkenyl which is unsubstituted or substituted by one or more fluorine atoms or trifluoromethyl groups, morpholino which may be substituted by $C_1$–$C_{16}$ alkyl, aryl, aralkyl, $C_2$–$C_8$ alkenyl, $C_3$–$C_8$ cycloalkyl, $C_5$–$C_8$ cyclo-alkenyl which is unsubstituted or substituted by one or more fluorine atoms or trifluoromethyl groups, piperazino which may be substituted by trifluoroacyl or trifluoromethanesulfonyl or aryl(trifluoromethyl), tetrahydropyridine, a group of formula B or C

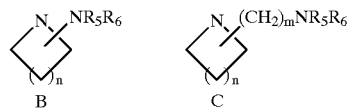

in which $R_5$ is hydrogen or $C_1$–$C_6$ alkyl, $R_6$ represents $COCF_3$ or $SO_2CF_3$, n and m, which are the same or different, are each an integer of from 1 to 4, or a saccharide of formula D as below defined

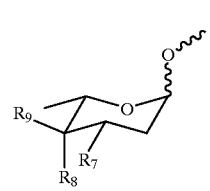

D wherein $R_7$ is hydrogen, hydroxyl, amino which is unsubstituted or substituted by acyl, trifluoroacetyl, trifluoromethansulfonyl, a residue of a naturally occurring amino acid, or a synthetic amino acid or a residue of di- or tri-peptide;

$R_8$ and $R_9$ are both hydrogen or one of $R_8$ or $R_9$ is hydroxyl, $C_1$–$C_4$ alkoxyl, tetrahydropyranyl, halogen or $OSO_2$ ($R_4$) as above defined and the other of $R_8$ and $R_9$ represents hydrogen or amino which is unsubstituted or substituted by acyl, trifluoroacetyl or trifluoromethansulfonyl;

Y is hydrogen, hydroxy, $C_1$–$C_{16}$ alkoxyl, amino which may be unsubstituted or substituted by acyl, trifluoroacetyl, $C_1$–$C_{16}$ alkyl, aryl or aralkyl which is unsubstituted or substituted by one or more fluorine atoms, morpholino, piperazino which may be substituted by trifluoroacyl or trifluoromethansulfonyl, tetrahydropyridine, a group of formula B or C as above defined, or a saccharide of formula D as above defined;

Z is C—O, CHOH or $CH_2$;

wherein at least one fluorine atom linked to the anthracyclinone or anthracycline skeleton or carried by groups linked at different positions of the molecule; or a pharmaceutically acceptable salt thereof; for the diagnosis of amyloidosis or in the preparation of a composition for such a diagnosis.

When $R_7$ is a residue of a naturally occurring amino acid, or a residue of a di- or tri-peptide, it is preferably in the form N-trifluoroacetyl or trifluoromethansufonyl.

Preferred compounds of formula A are those wherein:

$R_1$ is hydrogen, hydroxyl, fluorine, methoxy, amino, aminotrifluoromethanesulfonyl ($NHSO_2CF_3$), aminotrifluoroacetyl, or O-mesyl [$OSO_2CH_3$];

$R_2$ is hydroxyl;

$R_3$ is $C_1$–$C_6$ mono- or bis-alkylamino which is unsubstituted or substituted by one or more fluorine atoms, benzyltrifluoroethylamino, morpholinyl, trifluoromethanesulfonylpiperazinyl, trifluoroacetylpiperazinyl, tetrahydropyridinyl, a group of formula B or C in which $R_5$ is hydrogen or methyl or ethyl, $R_6$ is $COCF_3$ or $SO_2CF_3$, n is 2 or 3, m is 2 or 3, or a saccharide of formula D wherein $R_7$ is amino, aminotrifluoroacetyl, aminotrifluoromethanesulfonyl, or α- or ε-N-trifluoroacetyl-lysine;

$R_8$ hydroxyl, iodine, or O-mesyl $R_9$ is hydrogen;

Y is hydrogen, hydroxy, methoxy, amino, $C_1$–$C_6$ mono- or bis-alkylamino which is unsubstituted or substituted by one or more fluorine atoms, benzyltrifluoroethylamino, morpholinyl, trifluoroacetylpiperazinyl, trifluoromethanesulfonylpiperazinyl, tetrahydropyridinyl, a group of formula B or C in which $R_5$ is hydrogen or methyl or ethyl, $R_6$ is $COCF_3$ or $SO_2CF_3$, n is 2 or 3, m is 2 or 3, or a saccharide of formula D wherein:

$R_7$ is amino, aminotrifluoroacetyl, aminotrifluoromethanesulfonyl, α- or ε-(N-trifluoroacetyl)-lysine, or α- or ε-(N-trifluoromethanesulfonyl)-lysine;

$R_8$ is hydroxyl, iodine, or O-mesyl [$OSO_2CH_3$];

$R_9$ is hydrogen;

Z is C=O or CHOH.

More preferred compounds of formula A are those wherein:

$R_1$ is hydrogen or methoxy;

$R_2$ is hydroxy;

$R_3$ is hydrogen, hydroxyl, hexafluorodiethylamine, benzyltrifluoroethylamino morpholino, trifluoromethanesulfonylpiperazine, trifluoroacylpiperazino, tetrahydropyridine, a group of formula B or C in which $R_5$ is hydrogen or methyl, $R_6$ is $COCF_3$, n is 2 or 3 m is 2 or 3 or a saccharide of formula D wherein $R_7$ is amino, aminotrifluoromethanesulfonyl, aminotrifluoroacetyl, or α- or ε-N-trifluoroacetyl-lysine;

$R_8$ is iodine;

$R_9$ is hydrogen;

Y is hydrogen, hydroxy, hexafluorodiethylamine, benzyltrifluoroethylamino morpholino, trifluoromethanesulfonylpiperazine, trifluoroacetylpiperazino, or a saccharide of formula B wherein $R_5$ is amino, aminotrifluoroacetyl, or α- or ε-N-trifluoroacetyl-lysine;

$R_6$ is iodine;

$R_7$ is hydrogen;

Z is C=O.

Further preferred compounds of the formula A are those wherein:

$R_1$ is methoxy;

$R_2$ is hydroxy;

$R_3$ is hydrogen, hydroxyl, hexafluorodiethylamine, benzyltrifluoroethylamino, morpholino, trifluoroacylpiperazino, or tetrahydropyridine;

Y is hydrogen, hydroxy, trifluoromethanesulfonylpiperazine, trifluoroacetylpiperazino, a group of formula B or C in which $R_5$ is hydrogen, $R_6$ is $COCF_3$, n is 3 m is 2 or a saccharide of formula D wherein $R_7$ is amino, aminotrifluoroacetyl, or α- or ε-N-trifluoroacetyl-lysine;

$R_8$ is iodine;

$R_9$ is hydrogen;

Z is C=O.

The term "alkyl" as employed herein includes both linear and branched chain radicals of up to 16 carbons, for example methyl, ethyl, propyl, isopropyl, butyl, t-butyl, isobutyl, pentyl, hexyl, isohexyl, heptyl, octyl, nonyl, decyl, undecyl, dodecyl, the various branched chain isomers thereof, as well as such groups including one or more halo substituent, such as fluorine, chlorine, bromine, iodine, $CF_3$, alkoxy substituent, an aryl substituent, an alkyl-aryl substituent, a haloaryl substituent, a cycloalkyl substituent or an alkyl-cycloalkyl substituent.

The term "alkenyl" as used herein includes both linear and branched chain radicals of up to 8 carbons, or example allyl, butenyl, hexenyl, octenyl.

The term "cycloalkyl" as used herein means a cycloalkyl group having 3 to 8 carbons, for example cyclopropyl, cyclopentyl, cyclopentylmethyl, cycloheptyl and cyclooctyl.

The term "aryl" as employed herein includes both monocyclic or bicyclic aromatic groups containing from 6 to 10 carbons in the ring portion, such as phenyl, naphthyl, substituted phenyl or substituted naphthyl, wherein the substituent on either the phenyl or naphthyl may be for example $C_{1-6}$ alkyl, halogen, $C_{1-6}$ alkoxy.

The term "halogen" as used herein means fluorine, chlorine, bromine and iodine.

The term "aralkyl" as used herein refers to alkyl groups as previously discussed having an aryl substituent, for example benzyl, phenethyl, diphenylmethyl and triphenylmethyl.

The term "alkoxy" includes any of the above alkyl groups linked to an oxygen atom.

This invention also includes all the possible isomers and mixture thereof, including diastereoisomeric mixtures and racemic mixtures, resulting from the possible combination of R and S stereochemical centres at C-7 and C-9 as well as α or β glycosidic linkage of the saccharide.

The present invention provides the salts of those compounds of formula A that have salt-forming groups, especially the salts of the compounds having a carboxylic group, a basic group (e.g. an amino group).

The salts are especially physiologically tolerable salts, for example alkali metal and alkaline earth metal salt (e.g. sodium, potassium, lithium, calcium and magnesium salts), ammonium salts and salts with an appropriate organic amine or amino acid (e.g. arginine, procaine salts), and the addition salts formed with suitable organic or inorganic acids, for example hydrochloric acid, sulfuric acid, carboxylic acid and sulfonic organic acids (e.g. acetic, trifluoroacetic, methanesulphonic, p-toluensulphonic acid).

The present invention encompasses all the possible stereoisomers as well as their racemic or optically active mixtures. Compounds of formula A are characterized by the presence of fluorine atoms or groups bearing fluorine atoms linked at different positions of the anthracycline skeleton. For example the fluorine atom may be linked at C-4 of the aglycone moiety or at C-4' of the sugar residue. Groups bearing fluorine atoms, for example the aminotrifluoroacetyl group, $NHCOCF_3$ or aminotrifluoromethane-sulfonyl, $NHSO_2$–$CF_3$, may be linked at different positions of the molecule such as: C-4, C-6 and C-11 of the aglycone portion of the anthracycline or C-3' or C-4' of the sugar residue. The trifluoroacyl or trifluoromethane-sulfonyl groups may be also carried by a substituent attached at C-14 of the aglycone such as the 14-[1-(4-trifluoroacyl)piperazine], or at C-3' of the sugar residue such as α- or 3'-N-[(ε-N-trifluoroacyl)-lysine]. Preferably, anthracyclines of formula A in which the amino sugar is in the form of N-acyl derivative, such as N-trifluoroacetyl or N-trifluoromethane-sulfonyl, are converted into water soluble derivatives by means of amino substituents attached at position C-14.

Several 3'-N-trifluoroacetyl derivatives of anthracyclines are known, for example those of 4-alkoxy-derivatives (see: U.S. Pat. No. 4,166,848 4.9.1979), or the 6-alkoxy-derivatives (see: U.S. Pat. No. 4,191,756 4.3.1980), or the 11-alkoxy-derivatives (see: U.S. Pat. No. 4,191,755 4.3.1980), or 4'-iodo derivatives (see: U.S. Pat. No. 4,345,070 17.8.1982), others were reported by F. Arcamone in *Doxorubicin,* Medicinal Chemistry, Vol. 17, Academic Press, 1981. The therapeutic use for the treatment of amyloidosis of some compounds of formula A has already been claimed in our PCT patent Applications WO96/04895 and WO96/07665.

The present invention also provides new compounds of formula A as defined above, and their therapeutic use in the treatment of amyloidosis, wherein:

$R_3$ is amino which is mono- or di-substituted by $C_{b\ 1}-C_{16}$ alkyl, aryl, aralkyl, $C_2-C_8$ alkenyl, $C_3-C8$ cycloalkyl, $C_5-C_8$ cyclo-alkenyl substituted by one or more fluorine atoms or trifluoromethyl groups, morpholino substituted by $C_1-C_{16}$ alkyl, aryl, aralkyl, $C_{2-C8}$ alkenyl, $C_3-C_8$ cycloalkyl, $C_5-C_8$ cyclo-alkenyl substituted by one or more fluorine atoms or trifluoromethyl groups, piperazino substituted by triflouroacyl or trifluoromethanesulfonyl or tetrahydropyridine, or a group of formula B or C

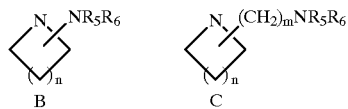

in which $R_5$ is hydrogen or $C_1-C_6$ alkyl, $R_6$ is $COCF_3$ or $SO_2CF_3$, n and m, which are the same or different, are each an integer of from 1 to 4.

The following specific compounds are new per se:

N-trifluoroacetyl-4'-iododoxorubicin (A1), 14-(4-trifluoroacetylpiperazin-1-yl)-daunomycinone (A2), 14-(4-trifluoromethanesulphonylpiperazin-1-yl)-daunomycinone (A3), 14-[4-(3-trifluoromethylphenyl)piperazin-1-yl]-daunomycinone (A4), 14-[N-ethyl-N-(3,5-bis-trifluoromethylphenyl)methyl] daunomycinone (A5), 14-[N-benzyl-N-(2,2,2-trifluoroethyl)] amino-daunomycinone (A6) and 14-(1,2,3,6-tetrahydropyridin-1-yl)-4'-deoxy-4'-iodo-3'-trifluoroacetyl daunorubicin (A7).

Fluoro-derivatives of general formula A may be prepared, following standard procedures described in the literature of anthracyclinones or anthracyclines, starting from compounds of formula E

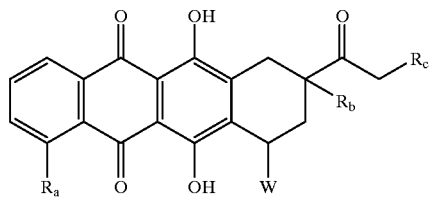

wherein:

$R_a$ is hydrogen, hydroxyl, methoxy, amino, $OSO_2(R_4)$ in which $R_4$ is as above defined;

$R_b$ is hydrogen or hydroxyl;

$R_c$ is hydrogen, bromine or hydroxyl.

W is hydrogen, hydroxyl or a residue of a saccharide of formula W'

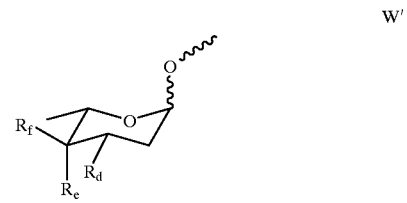

in which $R_d$ is hydrogen, hydroxyl or amino, $R_e$ and $R_f$ are both hydrogen or one of $R_e$ or $R_f$ is hydroxyl alkoxyl, halogen or $OSO_2(R_4)$ as above defined and the other of $R_e$ or $R_f$ is hydrogen or amino.

In particular, compounds of formula A wherein $R_3$ is an amino containing group which bears fluorine atoms, may be prepared by reacting the 14-bromo derivatives of formula E ($R_c$=Br), prepared as described in J.Org.Chem., 42 3653 (1977) from the corresponding compound of formula E in which $R_c$ is hydrogen, with a mono or di-substituted amino compound in aprotic organic solvent, such as methylene chloride or acetone or dimethyl-formamide or tetrahydrofurane, at temperature from 4° C. to 40° C. and from 4 to 48 hours. Preferred conditions encompass use of an excess of amine from 2 to 5 folds respect to the 14-bromo derivative, use of methylene chloride as solvent, at room temperature for 24 hours. The resultant 14-amino derivative may be, if necessary, reacted with an appropriate reagent, such as trifluoromethansulphonyl or trifluoroacetic anhydride, for introducing the desired fluoro bearing group.

In another example: compounds of formula A bearing a trifluoro-acetyl group, such as those in which $R_7$ is the group $NHCOCF_3$, may be prepared by reacting the corresponding anthracyclines of formula E in which $R_d$ is an amino group with trifluoroacetic anhydride, in aprotic organic solvents, such as dry methylene chloride, at 0° C. from 15 minutes to 3 hours.

An embodiment of the starting anthracyclinones or anthracyclines for the preparation of fluoro derivatives of formula A comprises: daunomycinone ($E_1$: $R_a$=$OCH_3$, W=OH, $R_b$=OH, $R_c$=H), 4-demethoxydaunomycinone ($E_2$: $R_a$=H, W=OH, $R_b$=OH, $R_c$=H), and their corresponding 14-bromoderivatives (E3 and E4 respectively in which $R_c$=Br), 7-deoxy derivatives (E5 and E6 respectively in which W=H), 7-deoxy and 14-bromo derivatives (E7 and E8 respectively in which W=H and $R_c$=Br) or 7-bromo derivatives (E9 and E10 respectively in which W=Br); the glycosides 4'-iododaunorubicin (E11: $R_a$=$OCH_3$, $R_{b=OH,}$ $R_c$=H, W=W' in which $R_d$=NH$_2$, $R_e$=I, $R_f$=H), 4'-iododoxorubicin (E12: $R_a$=OCH$_3$, $R_b$=$R_c$=OH, W=W' in which $R_e$=NH$_2$, $R_f$=I, $R_g$=H)

All these compounds are well known from the literature.

Binding of anthracyclinones and anthracyclines to Aβ fibrils

Fibrils from Aβ25–35 peptide are suspended in a solution of 10% dimethylsulfoxide in distilled water containing the test compound at various concentrations and incubated at room temperature for 60 minutes. After incubation, the samples are centrifuged at 15000 g for 10 minutes at room temperature and the supernatant withdrawn. Fibril pellets are washed three times with 0.3 ml of 10% DMSO in distilled water, dissolved in ethanol and the bound compound is quantified by fluorescent detection. EC$_{50}$ are then calculated using rectangular hyperbola (binding isotherm) equation and represents the affinity of the test compounds for the Aβ fibrils.

The compounds of the present invention have EC$_{50}$ comparable to that of iododoxorubicin (IDOX), which was used as reference compound (see WO95/04538). The following data are reported as example.

IDOX EC$_{50}$=52.04 ±10.66 μM

Compound A3 EC$_{50}$8.16±1.32 μM

Aβ1–40 peptide monomer is dissolved in Tris.HCl buffer 100 mM pH 7.4 and incubated for 5 days at 37° C. The precipitated fibrils are centrifuged, washed with distilled water, centrifuged again and resuspended in distilled water at a concentration of 230 monomer-equivalent. The fibril suspension is sonocated for one minute and freezed at −20° C. in aliquots until use. Binding studies are initiated by the addition of 33 μl of a 230 μM suspension of Aβ1–40 fibrils to a solution of the test compound in water, containing 3% (v/v) of dimethylsulfoxide, at various concentrations so as to obtain a final volume of 100 μl. The resulting suspension is incubated at room temperature for 15 minutes. After incubation, the suspension is loaded onto a Millipore ultrafree MC filter (0.22 μm pore retention) and centrifuged for 5 minutes at 4° C. The filter is washed two times with 100 μl of distilled water and the bound compound is recovered from the filter by washing the filter with 100 μl of a mixture of 0.6M hydrochloric acid/ethanol 50:50 (v/v). The amount of bound compound is quantified by HPLC. The aspecific binding of the compounds to the filter is evaluated by processing samples of the compounds, as previously described, in the absence of fibrils. The amount of compound bound to the filter is subtracted from the total binding value obtained in the presence of fibrils. Binding parameters were estimated by computerised non-linear regression analysis according to the Hill equation. Data are expressed as nanomoles of compound bound per mg of peptide monomer (B$_{max}$)

The following data are reported as example.

IDOX B$_{max}$=122.2 nmoles/mg Aβ1–40

Compound A5 B$_{max}$=223.1 nmoles/mg Aβ1–40

The compounds of the present invention are also endowed with antifibrillogenic activity. When Aβ peptides are incubated with the compounds, a reduction in the formation of amyloid fibrils is observed. The amount of amyloid that results from peptide aggregation can be evaluated using the thioflavine T (ThT) assay as reported in the literature by Naiki et al., *Analytical Biochemistry* 1989, vol. 177, p. 244 and by H. LeVine III, *Protein Science* 1993, vol.2, p. 404. Compounds are incubated at a concentration of 30 μM, in 50 μM phosphate buffer pH 5 at 25° C. during 24 hours, with 100 μM peptide. The incubated samples are then diluted with sodium citrate buffer pH 5 containing 47 μM ThT.

Fluorescence was measured with excitation at 420 nm and emission at 490 nm in a Kontron fluorescence spectrophotometer and the values were averaged after subtracting the background fluorescence of ThT. The less the fluorescence the less the amount of amyloid formed during the incubation period.

The following data obtained with the Aβ25–35 peptide are reported as examples.

| COMPOUND | ThT fluorescence (% of control) |
|---|---|
| iododoxorubicin | 40.95 |
| A1 | 20.58 |
| A2 | 22.24 |
| A3 | 23.00 |
| A4 | 22.27 |
| A5 | 23.05 |
| A6 | 34.99 |
| A7 | 33.24 |

As stated above, the compounds of the present invention are able to bind to fibrils and amyloid deposits and plaques from amyloidogenic peptides. In the case of Alzheimer disease, amyloid deposits are of Aβ1–40 or Aβ1–42(3), see Gravina S. A. et al., Journal of Biological Chemistry, 1995, vol. 270, p. 7013. The $^{19}$F atoms that are contained in the compounds can be detected by Nuclear Magnetic Resonance (NMR) spectroscopy: therefore, the said compounds can find application in the in vivo detection of amyloid deposits and plaques thus allowing to diagnose and to monitor the progression of diseases associated with the formation and deposition in different organs and tissues of amyloid proteins as it is the case in primary and secondary peripheral, systemic and central amyloidoses, such as, for example, Alzheimer disease, Down syndrome, spongiforme encephalopaty. Compounds of this invention can also find application in monitoring the effects of therapy on all amyloidogenic diseases.

The present invention also relates to methods of using the described compounds for $^{19}$F magnetic resonance imaging (MRI). Such methods comprise administering to a living subject an effective amount of a $^{19}$F-labelled compound and then detecting the $^{19}$F NMR signal produced thereby.

The present invention also includes, within its scope, pharmaceutical compositions comprising one or more, new or known, compounds of formula A as active ingredients, in association with pharmaceutically acceptable carriers, excipients or other additives, if necessary, for use in a diagnostic method or in the treatment of amyloidosis. In the diagnosis or treatment of amyloidosis, a compound of formula A or a pharmaceutically acceptable salt thereof is typically administered to a patient in an amount of from 0.1–50mg/kg body weight.

The following Examples illustrate the invention without limiting it.

EXAMPLE 1
N-trifluoroacetyl-4'-iododoxorubicin (A1)

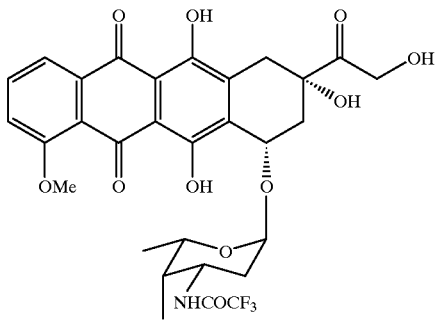

4'-iododoxorubicin hydrochloride (E12: 0.7 g, 1 mmol) is suspended in anhydrous methylene chloride (50 ml), cooled at 0° C. and added dropwise, in 5 minutes under stirring, with a solution of trifluoroacetic anhydride (0.26 ml, 0.2 mmol) in dry methylene chloride (5 ml). The mixture is kept under stirring for 30 minutes, then aqueous sodium hydrogen carbonate (20 ml of 5% solution) is added. After 15 minutes, the organic phase is separated, washed with water (50 ml), dried over anhydrous sodium sulphate and concentrated to small volume under reduced pressure. The title compound A1 (0.7 g) is recovered by adding ethyl ether/hexane (1:1 v/v).

TLC on Kieselgel $F_{254}$ (Merck), eluting system methylene chloride: acetone (95:5 by volume) $R_f$=0.53 FD-MS: m/e 748 [M]$^+$ $^1$HNMR (200 MHz, CDCl$_3$) δ:

1.30(d, J=6.1 Hz, 3H, CH$_3$–5'); 1.84 (dd, J=4.6 13.4 Hz, 1H, H-2'eq); 2.05 (m, 1H, H-2'ax); 2.24 (dd, J=4.2, 14.9Hz, H-8ax) 2.36 (ddd, J=1.5, 2.2, 14.9 Hz, 1H, H-8 eq) ; 2.99 (s, J=5.0 Hz, 1H, CH$_2$OH); 3.05 (d, J=1.5, 18.9 Hz, 1H, H-10 eq); 3.42 (dq, J=1.5, 6.1 Hz, 1H, H-5'); 3.60 (m, 1H, H-3'); 4.09 (s, 1H, 4-OCH$_3$); 4.28 (s, 1H, OH-9); 4.61 (m, 1H, H-4'); 4.77 (d, J=5.0 Hz, 2H, CH$_2$-14); 5.30 (dd, J=2.2, 4.2 Hz, 1H, H-7); 5.52 (d, J=8.3 Hz, 1H, NH=CO); 7.40 (dd, J=1.1, 8.6 Hz, H-3); 7.79 (dd, J=7.7, 8.6 Hz, H-2); 8.04 (dd, J=1.1, 7.7 Hz, 1H, H-1); 13.24 (s, 1H, OH-11) ; 14.00 (s, 1H, OH-6).

EXAMPLE 2
14-(4-trifluoroacetylpiperazin-1-yl)-daunomycinone (A2)

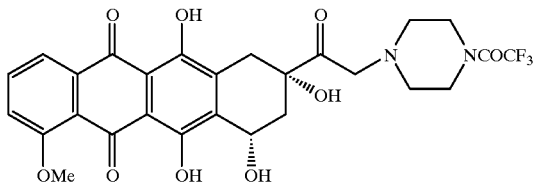

14-Bromodaunomycinone (E3, 3.2 g, 6.9 mmol), prepared as described in J. Org. Chem., 42, 3653 (1977), is dissolved in dry methylene chloride (200 ml), treated with anhydrous piperazine (1.19 g, 13.8 mmol) and kept at room temperature for 18 hours.

The solvent is then removed under reduced pressure and the crude product is flash chromatographated on silica gel eluting with a mixture of methylene chloride-methanol-acetic acid (90:10:0.3 by volume) to give 14-(N-piperazinyl) daunomycinone (0.9 g, yield 27%). FAB-MS: m/z 483 [M+H]$^+$; m/z 447 [M+H-2H$_2$O]$^{+1}$H-NMR (200 MHz, CDCl$_3$) δ; 2.14 (dd, J=5.0, 14.8 Hz, 1H, H-8ax); 2.36 (ddd, J=2.0, 2.2, 14.8 Hz, 1H, H-8 eq); 2.59, 2.98 (two multiplets, 8H, N(CH$_2$CH$_2$)$_2$NH; 2.97 (d, J=18.7 Hz, 1H, H-10ax); 3.16 (dd, J=2.0, 18.7 Hz, 1H, H-10 eq); 3.58, 3.69 (two doublets, J=16.5 Hz, 2H, CH$_2$-14) ; 4.08 (s, 3H, OCH$_3$) ; 5.26 (dd, J=2.2, 5.0 Hz, 1H, H-7); 7.38 (dd, J=0.9, 8.6 Hz, 1H, H-3); 7.77 (dd, J=7.7, 8.6 Hz, 1H, H-2); 8.01 (dd, J=1.1, 7.7 Hz, 1H, H-1).

A solution of 14-(N-piperazinyl)daunomycinone (0.35 g, 0.7 mmol) and triethylamine (0.2 g, 1.4 mmol) in 30 ml of methylene chloride is treated with trifluoroacetic anhydride (0.1 g, 0.7 mmol) and stirred at room temperature for 1 hour. The reaction mixture is diluted with methylene chloride, washed with water and dried on anhydrous sodium sulphate. The solvent is then removed under reduced pressure and the residue is flash chromatographated on silica gel, eluting with a mixture of methylene chloride and methanol (8:2 by volume), to give the title compound A2 which is converted into the corresponding hydrochloride (0.23 g, yield 50%) by addition of the stoichiometric amount of methanolic hydrogen chloride followed by precipitation with ethyl ether.

TLC on Kieselgel $F_{254}$ (Merck), eluting system methylene chloride/methanol/acetic acid/water (60:8:2:1 by volume), $R_f$=0.57. FAB-MS: m/z 579 [M+H]$^+$; m/z 562 [M+H–H$_2$O]$^+$ $^1$H-NMR (200 MHz, DMSO-d6) δ; 2.03 (dd, J=4.0, 14.3 Hz, 1H, H-8ax) ; 2.30 (m, 1H), H-8 eq); 2.90, 3.14 (two doublets, J=18.0 Hz, 2H, CH$_2$-10); 3.0–4.0 (m, 8H, N(CH$_2$CH$_2$)$_2$N); 3.98 (s, 3H), OCH$_3$); 4.77 (m, 2H), CH$_2$-14); 5.12 (m, 1H, H-7); 6.30 (broad signal, 1H, OH-9); 7.64 (m, 1H, H-3); 7.90 (m, 2H, H-1+H+2); 10.60 (broad signal, 1H, NH$^+$); 13.26 (s, 1H, OH-11); 13.97 (s, 1H, OH-6)

EXAMPLE 3
14- (4-trifluoromethanesulphonylpiperazin-1-yl) -daunomycinone (A3)

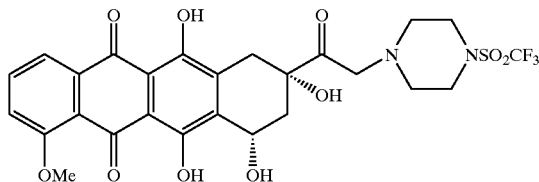

A solution of 14-(N-piperazinyl)daunomycinone (0.35 g, 0.7 mmol), prepared as described in Example 2 and triethylamine (0.2 g, 1.4 mmol) in methylene chloride (30 ml) is treated with trifluoromethansulphonyl anhydride (0.1 g, 0.7 mmol) and stirred at room temperature for 1 hour. The reaction mixture is diluted with methylene chloride, washed with water and dried on anhydrous sodium sulphate. The solvent is then removed under reduced pressure and the residue is flash chromatographated on silica gel, eluting with a mixture of methylene chloride and methanol (8:2 by volume), to give the title compound A3 which is converted into the corresponding hydrochloride (0.11 g, yield 23%) by addition of the stoichiometric amount of methanolic hydrogen chloride followed by precipitation with ethyl ether.

TLC on Kieselgel $F_{254}$ (Merck), eluting system methylene chloride/methanol/acetic acid/water (60:8:2:1 by volume), $R_f$=0.62. FAB-MS: m/z 615 [M+H]$^+$; m/z 597 [M+H–H$_2$O]$^+$ $^1$H-NMR (200 MHz, DMSO-d6) δ: 2.02 (dd, J=4.0, 14.3 Hz, 1H, H-8ax); 2.27 (m, 1H, H-8 eg); 2.93, 3.11 (two doublets, J=18.5 Hz, 2H, CH$_2$-10); 3.2–4.0 (m, 8H, N(CH$_2$CH$_2$)$_2$N); 3.99 (s, 3H), OCH$_3$); 4.60 (m, 2H, CH$_2$-14); 5.13 (m, 1H, H-7); 7.66 (m, 1H, H-3); 7.93 (m, 2H, H-1+H-2); 13.28 (s, 1H, OH-11; 13.98 (s, 1H, OH-6)

EXAMPLE 4
14-[4-(3-trifluoromethylphenyl)piperazin-1-y]-daunomycinone (A4)

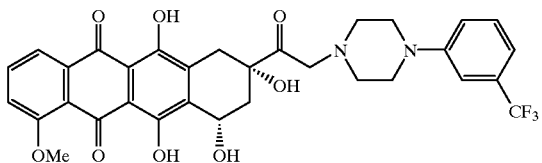

14-bromodaunomycinone (E3, 1 g, 2.1 mmol), prepared as described in J. Org. Chem., 42, 3653 (1977), is dissolved in dry methylene chloride (125 ml), treated with 1-(3-trifluoromethyl-phenyl) piperazine (1 g, 4.4 mmol) and kept at room temperature for 42 hours. The solvent is then removed under reduced pressure and the crude product is flash chromatographated on silica gel eluting with a mixture of chloroform-methanol (98:2 by volume) to give the title compound A4 (1.02 g, yield 78%) which is converted into the corresponding hydrochloride by addition of the stoichiometric amount of methanolic hydrogen chloride followed by precipitation with ethyl ether. FAB-MS: m/z 627 [M+H]$^+$; m/z 619 [M+H$_2$O]$^+$. $^1$H-NMR (200 MHz, DMSO-d6) δ: 2.06 (dd, J=4.0, 14.3 Hz, 1H, H-8 ax); 2.28 (m, 1H, H-8 eq); 2.96, 3.14 (two doublets, J=18.7 Hz, 2H, CH$_2$-10); 3.2–4.0 (m, 8H, N(CH$_2$CH$_2$)$_2$N; 3.99 (s, 3H, OCH$_3$); 4.90 (m, 2H, CH$_2$-14); 5.17 (m, 1H, H-7); 5.70 (broad signal, 1H, OH-7); 6.28 (s, 1H, OH-9); 7.1–7.5 (m, 4H, m.CF$_3$-C$_6$H$_{44}$); ⁻7.67 (m, 1H, H-3); 7.92 (m, 2H, H-1 +H-2); 10.2 (broad signal, 1H, NH$^+$); 13.29 (s, 1H, OH-11); 14.00 (s, 1H, OH-6).

EXAMPLE 5
14-[N-ethyl-N-(3,5-bis-trifluoromethylphenyl) methyl] daunomycinone (A5)

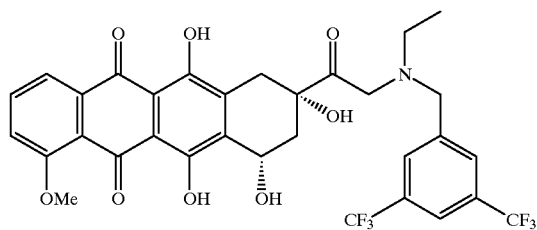

14-Bromodaunomycinone (E3, 0.5 g, 1.05 mmoles) is added portionwise, over 75 minutes, to a solution of N-ethyl-N-(3,5-ditrifluoromethylphenyl)methylamine (0.34 g, 1.25 mmoles) and di-isopropylethylamine (0.215 ml, 1.26 mmoles) in dry N,N-dimethyl-acetamide (3 ml) at 60° C. The reaction mixture is kept at 60° C. for additional 30 minutes. The solvent is then removed under reduced pressure and the residue is taken up with brine and extracted with ethyl acetate. The extracts are washed with water, dried over anhydrous sodium sulphate, and the solvent is evaporated. The raw material is purified by silica gel column chromatography (chloroform/methyl alcohol 98:2) to give the title compound A5 as a red powder (0.21 g, yield 30%) which is converted into the corresponding hydrochloride by addition of the stoichiometric amount of methanolic hydrogen chloride followed by precipitation with ethyl ether. FAB3-MS: m/z 668 [M+H]$^{30}$ ⁻; m/z 650 [M+H–H$_2$O]$^+$; m/z 632 [M–2H$^2$O–H]$^+$. $^1$H-NMR (200 MHz, DMSO-d6) δ: 1.07 (t, J=7.3 Hz, 3H, CH$_2$CH$_3$); 1.6–3.6 (m, 6H, CH$_2$CH$_3$+CH$_2$-8+CH$_2$-10); 3.99 (s, 3H, OCH$_3$); 4.60 (m, 2H, NCH$_2$PH), 4.83 (m, 2H, CH$_2$-14); 5.07 (m, 1H, H-7); 5.5, 6.3 (broad signal, 2H, OH-7+OH-9); 7.65 (m, 1H, H-3); 7.92 (m, 2H, H-1+H-2); 8.24, 8.36 (two singlets, 3H, aromatic hydrogens); 10.14 (broad signal, 1H, NH$^+$) ; 13.24 (s, 1H, OH-11); 13.96 (s, 1H, OH-6).

EXAMPLE 6
14-[N-benzyl-N-(2,2,2-trifluoroethyl)]amino-daunomycinone (A6)

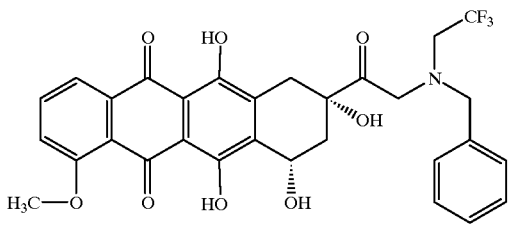

14-bromo-daunomycinone (0.70 g, 1.47 mmoles) is added portionwise over 75 min to a solution of benzyl-(2,2,2-trifluoroethyl)amine (0.554 g, 2.93 mmoles) and diisopropylethylamine (0.25 ml, 1.46 mmoles) in dry N,N-dimethylacetamide (3 ml) at 60° C. The reaction mixture is maintained at 60° C. for additional 30 min. The solvent is removed under reduced pressure and the residue is taken up with brine and extracted with ethyl acetate. The extracts are washed with water, dried over sodium sulphate, and the solvent is evaporated to leave 0.46 g of raw material which is purified by silica gel column chromatography (chloroform/methyl alcohol 99:1) to give the title compound as a red powder (60 mg), that was converted into the corresponding hydrochloride by addition of the stoichiometric amount of methanolic hydrogen chloride followed by precipitation with ethyl ether. FAB-MS: m/z 586 [M+H]$^+$; m/z 568 [M+H–H$_2$O]$^{+;\ m/z}$ 550 [M-2H$_2$O]$^+$; m/z 516 [M–CF$_3$]$^+$. $^1$H-NMR (200 MHz, DMSO-d6) δ: 1.8–2.2 (m, 2H, CH$_{2-8}$); 2.83–2.99 (two doubles, J=18.7 Hz, 2H, CH$_2$-10); 3.52 (q, J=10.1 Hz, 2H, NCH$_2$CF$_3$); 3.98 (s, 3H, OCH$_3$) 3.8–4.2 (m, 4H, NCH$_2$Ph+CH$_2$-13); 5.04 (m, 1H, H-7); 5.39 (d, J=6.8 Hz, 1H, OH-7); 7.1–7.4 (m, 5H, Ph); 7.6–7.8 (m, 3H, H–1+H+3); 13.2–13.9 (two bs, 2H, OH-6+OH-11).

EXAMPLE 8
14-(1,2,3,6-tetrahydropyridin-1-yl)-4'-deoxy-4'-iodo-3'-N-trifluoroacetyl daunorubicin (A7)

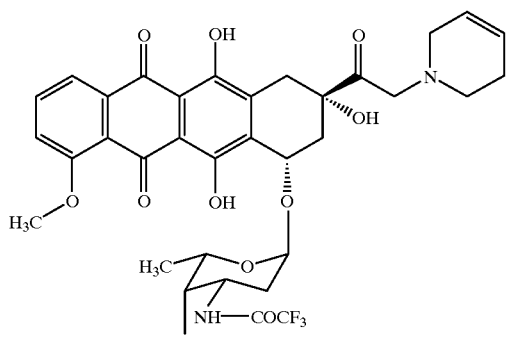

4'-deoxy-4'-iododaunorubicin (E11: 500 mg, 0.742 mmol.) is converted into the corresponding 14-bromo derivative following standard procedures (described in U.S. Pat. 3,803,124, Apr. 9, 1974). The compound is dissolved in acetone (10 ml), 1,2,3,6-tetrahydropyridine (0.5 ml, 5 mmol.) is added and the reaction is stirred at 35° C. during one hour. The reaction mixture is taken up with methylene chloride and water, the organic phase is separated, dried over anhydrous sodium sulphate and hexane is added to precipitate the crude product. Flash chromatography purification on silica gel of the precipitated product, using a mixture of methylene chloride/methanol/acetic acid (30:4:1) as the eluant, gives the pure compound which is converted into its hydrochloride salt by treatment with methanolic hydrochloric acid (160 mg, 28% yield). TLC (Kieselgel $F_{254}$ plates): eluting system methylene chloride/methanol/acetic acid/water 60:8:2:1 (v/v), $R_f$=0.25.

14-(1,2,3,6-tetrahydropyridin-1-yl)-4'-deoxy-4'-iododaunorubicin (70 mg, 0.1 mmol) is converted into the corresponding 3'-N-trifluoroacetyl derivative by treatment with trifluoroacetic anhydride (0.2 ml, 1.4 mmol) at 0° C. for one hour following standard procedures (see: F. Arcamone et al., *Chim. Ind.* (Milan), 1969, vol. 51, p. 834). The reaction mixture is flash chromatographated on silica gel using a mixture of methylene chloride/acetone (9:1 by volume). The purified product is converted into the hydrochloride salt by treatment with methanolic hydrogen chloride to give 46 mg (58% yield) of the desired product. TLC (Kieselgel $F_{254}$ plates): eluting system methylene chloride/acetone 80:20 (v/v), $R_f$=0.50. FAB-MS: m/z 815 [MH]$^+$; 462 [MH-sugar-$H_2O$]$^+$; 444 [MH-sugar-$2H_2O$]$^{+\cdot}$ $^1$H NMR (400 MHz, DMSO-$d_6$) δ; 1.15 (d, J=6.0 Hz, 3H, $CH_3$-5'); 1.56 (dd, J=3.8, 14.1 Hz, 1H, H-2'eq); 2.06 (m, 1H, H-2'ax); 2.23 (m, 2H, $CH_2$-8); 2.40 (m, 2H, N—$CH_2CH_2$—CH=CH); 2.95, 3.14 (two d, J=18.0 Hz, 2H, $CH_2$-10); 3.30 (m, 2H, N—$CH_2CH_2$+CH=CH); 3.50 (m, 1H, H-3'); 3.60 (m, 1H, H-5'); 3.70 (m, 2H, N—$CH_2$-CH=CH); 3.99 (s, 3H, $OCH_3$); 4.59, 4.72 (two d, J=18.8 Hz, 2H, $CH_2$-14); 4.79 (s, 1H, H-4'); 5.04 (m, 1H, H-7) 5.29 (d, J=3.4 Hz, 1H, H1'); 5.69, 5.90 (two d, J=10.7 Hz, 1H, CH=CH); 5.98 (s, 1H, OH-9); 7.64, 7.91 (two m, 3H, H-1, H-2, H-3); 9.51 (d, J=5.6 Hz, 1H, $NHCOCF_3$) ; 9.96 (broad signal, 1H, NH$^+$); 13.28 (s, 1H, OH-11); 14.05 (s, 1H, OH-6).

What is claimed is:

1. A method of diagnosing amyloidosis, comprising:
   administering to a subject a compound represented by formula A, or a pharmaceutically acceptable salt thereof:

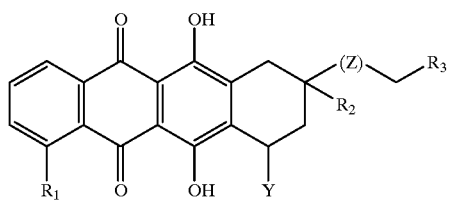

A wherein the compound represented by formula A interacts with amyloid deposits and plaques and with fibrils of amyloid, when present in the subject; and
   detecting the presence of $^{19}$F atoms contained in the compound represented by formula A by Nuclear Magnetic Resonance Spectroscopy,
   wherein
   $R_1$ is hydrogen, hydroxyl, halogen, $C_1$–$C_8$ alkoxyl, amino which may be substituted by benzyl, acyl or trifluoroacetyl, or $OSO_2(R_4)$ wherein $R_4$ is alkyl or aryl each of which is unsubstituted or substituted by one or more fluorine atoms;
   $R_2$ is hydrogen, or hydroxy;
   $R_3$ is hydrogen, hydroxyl,
   amino which may be mono- or di-substituted by $C_1$–$C_6$ alkyl, aryl, aralkyl, $C_2$–$C_8$ alkenyl, $C_3$–$C_8$ cycloalkyl, $C_5$–$C_8$ cyclo-alkenyl which is unsubstituted or substituted by one or more fluorine atoms or trifluoromethyl groups,
   morpholino which may be substituted by $C_1$–$C_6$ alkyl, aryl, aralkyl, $C_2$–$C_8$ alkenyl, $C_3$–$C_8$ cycloalkyl, $C_5$–$C_8$ cyclo-alkenyl which is unsubstituted or substituted by one or more fluorine atoms or trifluoromethyl groups,
   piperazino which may be substituted by trifluoroacyl or trifluoromethanesulfonyl or aryl(trifluoromethyl),
   tetrahydropyridine,
   a group of formula B or C

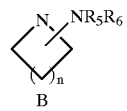 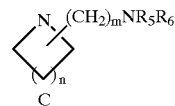

B      C wherein $R_5$ is hydrogen or $C_1$–$C_6$ alkyl, $R_6$ represents $COCF_3$ or $SO_2CF_3$, n and m, which are the same or different, are each an integer of from 1 to 4; or a saccharide of formula D:

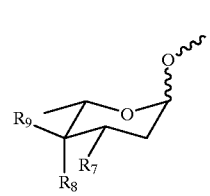

D wherein
   $R_7$ is hydrogen, hydroxyl, amino which is unsubstituted or substituted by acyl, trifluoroacetyl, trifluoromethanesulfonyl, a residue of a naturally occurring amino acid, or a synthetic amino acid or a residue of di- or tri-peptide;
   $R_8$ and $R_9$ are both hydrogen or one of $R_8$ or $R_9$ is hydroxyl , $C_1$–$C_4$ alkoxyl, tetrahydropyranyl, halogen or $OSO_2$ ($R_4$) above defined above and the other of $R_8$ and $R_9$ is hydrogen or amino which is unsubstituted or substituted by acyl, trifluoroacetyl or trifluoromethanesulfonyl;
   Y is hydrogen, hydroxy, $C_1$–$C_{16}$ alkoxyl, amino which may be unsubstituted or substituted by acyl, trifluoroacetyl, $C_1$–$C_{16}$ alkyl, aryl, or aralkyl which is unsubstituted or substituted by one or more fluorine atoms, morpholino, piperazino which may be substituted by trifluoroacyl or trifluoromethanesulfonyl, tetrahydropyridine, a group of formula B or C as defined above, or saccharide of formula D as defined above; and
   Z is C=O, CHOH, or $CH_2$;
   wherein at least one fluorine atom is linked to the anthracyclinone or anthracycline skeleton or is carried by groups linked at different positions of the molecule.

2. The method of claim 1, wherein
   $R_1$ is hydrogen, hydroxyl, fluorine, methoxy, amino, $NHSO_2CF_3$, aminotrifluoroacetyl, or $OSO_2CH_3$
   $R_2$ is hydroxyl;
   $R_3$ is $C_1C_6$ mono- or bis-alkylamino which is unsubstituted or substituted by one or more fluorine atoms or trifluoromethyl group, benzyltrifluoroethylamino, morpholinyl, trifluoromethanesulfonylpiperazinyl, trifluoroacetylpiperazinyl, tetrahydropyridinyl, a group of the formula B or C as defined above, wherein $R_5$ is hydrogen or methyl or ethyl, $R_6$ is $COCF_3$ or $SO_2CF_3$, n is 2 or 3, m is 2 or 3, or a saccharide of formula D as defined above, wherein $R_7$ is amino, aminotrifluoroacetyl, aminotrifluoromethanesulfonyl, or α- or ε-N-trifluoroacetyl-lysine;

$R_8$ is hydroxyl, iodine, or O-mesyl $R_9$ is hydrogen;

Y is hydrogen, hydroxy, methoxy, amino, $C_1$–$C_6$ mono-bis-alkylamino which is unsubstituted or substituted by one or more fluorine atoms, benzyltrifluoroethylamino morpholinyl, trifluoroacetylpiperazinyl, trifluoromethanesulfonylpiperazinyl, tetrahydropyridinyl, a group of formula B or C as defined above, wherein $R_5$ is hydrogen or methyl or ethyl, $R_6$ is $COCF_3$ n is 2 or 3, m is 2 or 3, or a saccharide of formula D as defined above, wherein $R_7$ is amino, aminotrifluoroacetyl, aminotrifluoromethanesulfonyl, α- or ε-(N-trifluoroacetyl)-lysine, or α- or ε-(N-trifluoromethanesulfonyl)-lysine;

$R_8$ is hydroxyl, iodine, or $OSO_2CH_3$;

$R_9$ is hydrogen; and

Z is C=O, or CHOH.

3. The method of claim 1 wherein $R_1$ is hydrogen or methoxy;

$R_2$ is hydroxy;

$R_3$ is hydrogen, hydroxyl, hexafluorodiethylamine, benzyltrifluoroethylamino, morpholino, trifluoromethanesulfonylpiperazine, trifluoroacetylpiperazino, tetrahydropyridine, a group of formula B or C as defined above, wherein $R_5$ is hydrogen or methyl, $R_6$ is $COCF_3$, n is 2 or 3 m is 2 or 3, or a saccharide of formula D as defined above, wherein $R_7$ is selected from the group consisting of amino, aminotrifluoromethanesulfonyl, aminotrifluoroacetyl, and α- or ε-N-trifluoracetyl-lysine;

$R_8$ is iodine;

$R_9$ is hydrogen;

Y is hydrogen, hydroxy, hexafluorodiethylamine, benzyl-trifluoroethylamino morpholino, trifluoromethanesulfonylpiperazine, trifluoroacetylpiperazino, or a saccharide of formula B as defined above, wherein $R_5$ is amino, aminotrifluoroacetyl, or α- or ε-N-trifluoracetyl-lysine;

$R_6$ is iodine;

$R_7$ is hydrogen; and

Z is C=O.

4. The method of claim 1, wherein $R_1$ is methoxy;

$R_2$ is hydroxy;

$R_3$ is hydrogen, hydroxyl, hexafluorodiethylamine, benzyltrifluoroethylamino, morpholino, trifluoroacylpiperazino, or tetrahydropyridine, Y is hydrogen, hydroxy, trifluoromethanesulfonylpiperazine, trifluoroacetylpiperazino, a group of the formula B or C as defined above, wherein $R_5$ is hydrogen, $R_6$ is $COCF_3$, n is 3 m is 2, or a saccharide of formula D as defined above, wherein $R_7$ is aminotrifluoroacetyl, or α-or ε-N-trifluoroacetyl-lysine;

$R_8$ is iodine;

$R_9$ is hydrogen; and

Z is C=O.

5. A compound represented by formula A, or a pharmaceutically acceptable salt thereof:

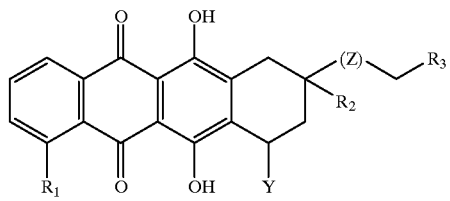

A wherein $R_1$ is hydrogen, hydroxyl, halogen, $C_1$–$C_8$ alkoxyl, amino which may be substituted by benzyl, acyl or trifluoracetyl, or $OSO_2$ ($R_4$), wherein $R_4$ is alkyl or aryl each of which is unsubstituted or substituted by one or more fluorine atoms;

$R_2$ is hydrogen, or hydroxy;

$R_3$ is amino which is mono- or di-substituted by $C_1$–$C_6$ alkyl, aryl, aralkyl, $C_2$–$C_8$ alkenyl, $C_3$–$C_8$ cycloalkyl, $C_5$–$C_8$ cyclo-alkenyl substituted by one or more fluorine atoms or trifluoromethyl groups, morpholino substituted by $C_{1-6}$-alkyl, aryl, aralkyl, $C_2$-$C_8$ alkenyl, $C_3$–$C_8$ cycloalkyl, $C_5$–$C_8$ cyclo-alkenyl substituted by one or more fluorine atoms or trifluoromethyl groups, piperazino substituted by trifluoroacyl or trifluoromethanesulfonyl, tetrahydropyridine, or a group of formula B or C:

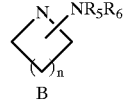 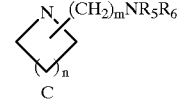

B    C in which $R_5$ is hydrogen or $C_1$–$C_6$ alkyl, $R_6$ is $COCF_3$ or $SO_2CF_3$, n and m, which are the same or different, are each an integer of from 1 to 4, Y is hydrogen, hydroxy, $C_1$–$Cl_6$ alkoxyl, amino which may be unsubstituted or substituted by acyl, trifluoracetyl, $C_1$–$C_{16}$ alkyl, aryl, or aralkyl which is unsubstituted or substituted by one or more fluorine atoms, morpholino, piperazino which may be substituted by trifluoroacyl or trifluoromethanesulfonyl, tetrahydropyridine, a group of formula B or C as defined above, or a saccharide of formula D:

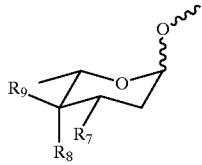

wherein

R$_7$ is hydrogen, hydroxyl, amino which is unsubstituted or substituted by acyl, trifluoracetyl, trifluoromethanesulfonyl, a residue of a naturally occurring amino acid, or a synthetic amino acid or a residue of di- or tri-peptide;

R$_8$ and R$_9$ are both hydrogen or one of R$_8$ or R$_9$ is hydroxyl, C$_1$–C$_4$ alkoxyl, tetrahydropyranyl, halogen or OSO$_2$ (R$_4$) above defined above and the other of R$_8$ and R$_9$ is hydrogen or amino which is unsubstituted or substituted by acyl, trifluoracetyl or trifluoromethanesulfonyl; and Z is C=O, CHOH, or CH$_2$.

6. The compound of claim 4, which is N-trifluoroacetyl-4'-iododoxorubicin, 14-(4-trifluoroacetylpiperazin-1-yl)-daunomycinone, 14-(4-trifluoromethanesulphonylpiperazin-1-yl)-daunomycinone, 14-[4-(3-trifluoromethylphenyl)piperazin-1-yl]-daunomycinone, 14-[N-ethyl-N-(3,5-bis-trifluoromethylphenyl)methyl] daunomycinone, 14-[N-benzyl-N-(2,2,2-trifluoroethyl)]amino-daunomycinone, or 14-(1,2,3,6-tetrahydropyridin-1-yl)-4'-deoxy-4'-iodo-3'-N-trifluoracetyl daunorubicin.

7. A pharmaceutical composition, comprising the compound of claim 4 and a pharmaceutically acceptable carrier or diluent.

8. A method of treating amyloidosis, comprising administering an effective amount of the compound of claim 4 to a patient in need thereof.

* * * * *

UNITED STATES PATENT AND TRADEMARK OFFICE
CERTIFICATE OF CORRECTION

PATENT NO. : 6,103,700
DATED : August 15, 2000
INVENTOR(S) : Tiziano Bandiera et al.

It is certified that error appears in the above-identified patent and that said Letters Patent is hereby corrected as shown below:

Title page,
Item [57],

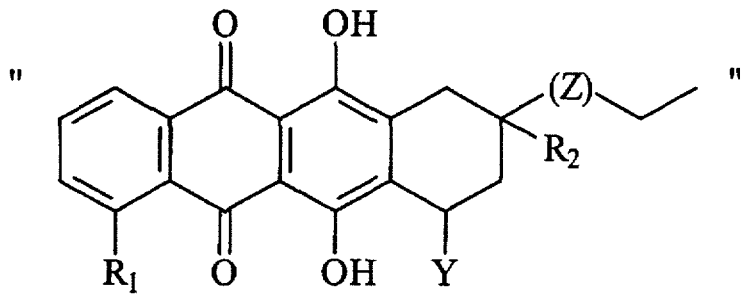

should read

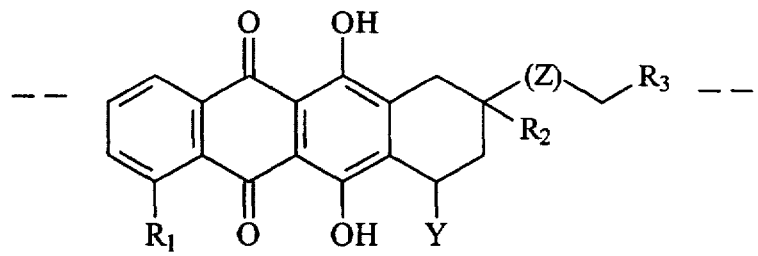

Column 2,
Line 43, "atom linked to" should read -- atom is linked to --.

Column 3,
Line 46, "trifluoroethylamino" should read -- trifluoroethylamino, --;
Line 48, "B" should read -- D --;
Line 50, "$R_5$" should read -- $R_7$ --;
Line 52, "$R_6$" should read -- $R_8$ --;
Line 53, "$R_7$" should read -- $R_9$ --.

UNITED STATES PATENT AND TRADEMARK OFFICE
CERTIFICATE OF CORRECTION

PATENT NO. : 6,103,700
DATED : August 15, 2000
INVENTOR(S) : Tiziano Bandiera et al.

It is certified that error appears in the above-identified patent and that said Letters Patent is hereby corrected as shown below:

Column 4,
Line 4, "2" should read -- 2 --;
Line 47, "group," should read -- group or --.

Column 5,
Line 29, "$C_{b1}$-$C_{16}$" should read -- $C_1$-$C_{16}$ --;
Line 33, "$C_{2-C8}$" should read -- $C_2$-$C_8$ --.

Column 6,
Last line, "$R_b=_{OH}$", should read -- $R_b$=OH --.

Column 15,
Line 60, "B" should read -- D --;
Line 62, "$R_5$" should read -- $R_7$ --;
Line 64, "$R_6$" should read -- $R_8$ --;
Line 65, "$R_7$" should read -- $R_9$ --.

Signed and Sealed this

Fourth Day of December, 2001

*Attest:*

NICHOLAS P. GODICI
*Attesting Officer*   *Acting Director of the United States Patent and Trademark Office*